United States Patent [19]

Holba et al.

[11] Patent Number: 4,577,492
[45] Date of Patent: Mar. 25, 1986

[54] ANALYTICAL METHOD AND APPARATUS

[75] Inventors: Albert G. Holba; Susanne B. Doe, both of Bartlesville; William B. Hughes, Osage County, all of Okla.

[73] Assignee: Phillips Petroleum Company, Bartlesville, Okla.

[21] Appl. No.: 652,155

[22] Filed: Sep. 18, 1984

Related U.S. Application Data

[63] Continuation of Ser. No. 493,842, May 12, 1983, abandoned.

[51] Int. Cl.[4] ............................................. G01N 31/08
[52] U.S. Cl. .............................. 73/61.1 C; 210/198.2; 422/70; 436/161
[58] Field of Search .................... 73/61.1 C; 422/70; 436/161; 210/198.2, 659

[56] References Cited

U.S. PATENT DOCUMENTS 4,271,697  6/1981  Mowery, Jr. ................. 73/61.1 C
4,446,105  5/1984  Dinsmore et al. ................. 422/70

OTHER PUBLICATIONS

Cole, E. R. and R. F. Bayfield, "Chromatographic Techniques in Sulfur Chemistry," In: Senning, A., ed., *Sulfur in Organic & Inorganic Chemistry*, vol. 2, (New York, Marcel Dekker, 1972), pp. 223-242.
Bollet, C. et al., "Rapid Separation of Heavy Petroleum Products by High-Performance Liquid Chromatography," *Journal of Chromatography*, 206 (1981), pp. 289-300.
Waters Technical Bulletin, "Rapid Hydrocarbon Group Separation of Crude Oil," Waters Associates, Milford, Mass., Sep. 1981.
Möckel, H. and B. Masloch, "LC-Determination of Elementary Sulphur," *Z. Anal. Chem.*, 281 (1976), pp. 379-380.
Radke, M. et al., "Preparative Hydrocarbon Group Type Determination by Automated Medium Pressure Liquid Chromatography," *Anal. Chem.*, 52 (1980), pp. 406-411.
Suatoni, J. C., "Hydrocarbon Group-Type Analysis by High Performance Liquid Chromatography," In: Altgelt, K. H. et al., eds., *Chromatography in Petroleum Analysis*, (New York, Marcel Dekker, 1979), pp. 122-136.
Werkhoven-Goewie, C. E. et al., "Liquid Chromatographic Detector for Organosulphur Compounds Based on a Ligand-Exchange Reaction," *Journal of Chromatography*, 203 (1981), pp. 165-172.

*Primary Examiner*—Stewart J. Levy
*Assistant Examiner*—Joseph W. Roskos
*Attorney, Agent, or Firm*—William R. Sharp

[57] ABSTRACT

A method and apparatus are provided for analysis of a sample of matter for multiple organic constituents and elemental sulfur in a single process. The method involves passage of a fluid sample through a first separations zone for retention of a first organic constituent, passage through a second separations zone for separation of the remaining organic constituents and sulfur, and quantitative determination of each constituent of interest including elemental sulfur.

20 Claims, 3 Drawing Figures

ULTRAVIOLET ABSORBANCE DETECTOR RESPONSE

ANALYTICAL METHOD AND APPARATUS

This is a continuation of application Ser. No. 493,842, filed May 12, 1983 now abandoned.

BACKGROUND OF THE INVENTION

In modern oil prospecting and reservoir analysis, geochemical methods are increasingly important and useful. Information relating to the location of an oil-bearing reservoir can be obtained from studies of rock samples obtained from target areas. Information on the type of oil present in the reservoir including its level of aromatic constituents and elemental sulfur, is important in assessing the production and refining techniques appropriate for the oil.

A method for analyzing such geochemical samples involves chromatographic separation of the organic constituents of the samples into chemical groups—polar compounds, aromatics, and saturates for example—and application of geochemical principles to the resulting chemical profiles to determine the type of reservoir or oil. A separate sample of soluble organic matter or oil from the same lot can also be examined for elemental sulfur, and the results used to further characterize the rock or oil under study.

It would be desirable to have a technique and apparatus for quickly and efficiently, in a single operation, analyzing a geological sample for both its constituent chemical groups and elemental sulfur.

It is therefore an object of the invention to provide a method for geochemical analysis of a sample of matter for constituent chemical groups and elemental sulfur. It is a further object to provide apparatus suitable for analyzing a sample of matter for its constituent chemical groups and elemental sulfur.

SUMMARY OF THE INVENTION

According to the invention, a method is provided in which a sample of matter is chromatographically separated into at least one constituent chemical group and elemental sulfur. The sample may contain at least one of the constituent groups selected from saturated hydrocarbons, aromatic compounds and polar compounds in addition to elemental sulfur. The method provides ior chromatographic separation of a constituent group of interest, detection of the constituent group by appropriate means, chromatographic separation of constituent elemental sulfur from the sample, and detection of the elemental sulfur by appropriate detecting means. In a specific embodiment, polar organic compounds are removed from a liquid sample on a chromatographic precolumn, aromatics, saturated hydrocarbons and elemental sulfur are separated on a separate column, the saturated hydrocarbons and elemental sulfur are quantitatively monitored, and then the polar compounds and aromatics are backflushed from their respective columns for quantitative determination.

Further according to the invention, apparatus is provided comprising means for introducing a liquid sample into a first separations zone comprising at least one adsorbent stationary phase suitable for separating and retaining a first organic constituent group of the sample, a second separations zone comprising at least one adsorbent stationary phase suitable for separating the sample into a second chemical constituent group of interest and elemental sulfur, detecting means for detecting a property of a chemical constituent group and/or sulfur representative of its quantity, and means for removing the first organic constituent group from the first separation means.

DETAILED DESCRIPTION OF THE INVENTION

Figure 1:
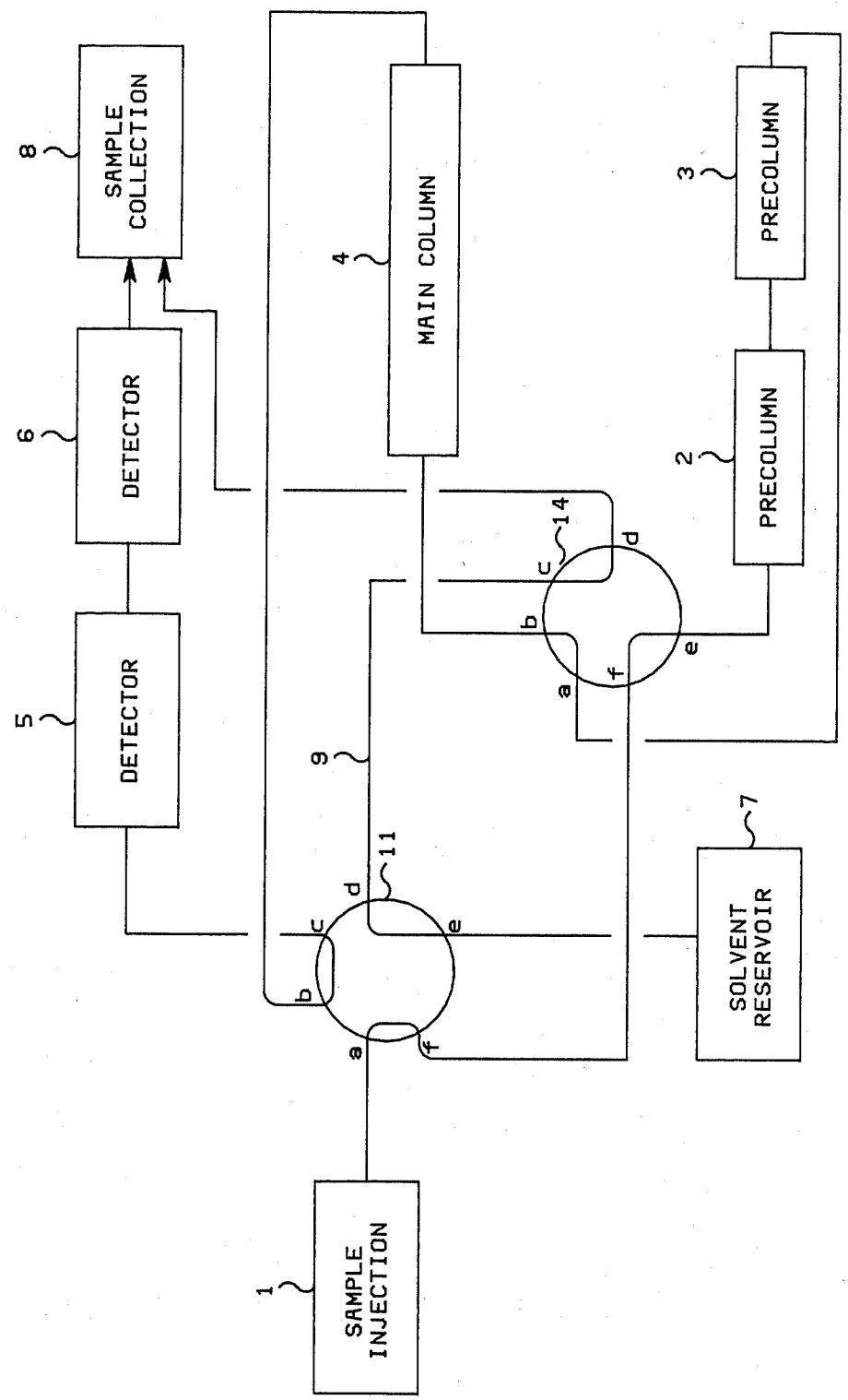
FIG. 1 is a schematic diagram showing one emhodiment of the invention.

The invention method and apparatus can be understood by reference to FIG. 1, which shows in schematic form the process according to a preferred embodiment of the invention. A liquid sample in a liquid mobile phase is introduced into a first precolumn 2 via sample injection means 1, ports a and f of switching valve 11 and ports f and e of switching valve 14.

The sample analyzed can be any organic chemical group containing material which also contains sulfur in elemental form. Samples for which the described invention method is particularly suitable include fractions of heavy petroleum products, soluble organic matter from rocks, coal liquids, refinery feedstreams and products, crude oil and lubricating oil. It is preferred to deasphalt the sample prior to analysis by the invention method.

The size of the sample will vary according to the equipment used in the system and the type of sample, but will generally range from about 1 mg to about 500 mg, with most samples being in the 10 mg to 150 mg range.

The organic chemical groups which can be separated and analyzed by the invention include saturated hydrocarbons (which will generally include monoolefins), aromatic hydrocarbons (which will generally include diolefins, thiophenes and furans), and polar organic compounds. Polar organic compounds are molecules which include a heteroatom such as nitrogen, sulfur, oxygen or a heavy metal. The polar compounds will exhibit various degrees of polarity, and it may be necessary or desirable in practicing the process to separate polar compounds into two or more groups. This can be accomplished, for example by including two or more adsorbent stationary phases in a separation zone of the invention apparatus.

The mobile phase can be any suitable liquid or liquid mixture inert to the sample constituents and the column packing and effective in carrying the sample constituents through the columns in the manner desired in the practice oi the invention. Suitable mobile phase liquids in liquid chromatography include n-hexane, cyclohexane, and methylene chloride for example. The mobile phase for backflushing can differ from the principal mobile phase in a given process according to the invention. n-Hexane is the preferred principal mobile phase and backflush liquid for the aromatics, and methylene chloride is the preferred backflush liquid for polar constituents.

Sample injection means 1 includes reservoirs for the mobile phase fluid(s) and means for introducing the sample into the analyzer and passing the mobile phase through the instrument at a controlled rate, as are known in the art of liquid chromatography.

The sample is passed via ports a and f of a first 6-port switching valve 11 and ports f and e of a second 6-port switching valve 14 to a first precolumn 2. The first precolumn contains a stationary phase material suitable for adsorbing a particular organic chemical group of interest or to retain a non-desired constituent from the sample. The choice of the stationary phase will depend upon the sample and the constituents to be removed or separated and identified. In a preferred embodiment of the invention in which polar compounds are retained on the first precolumn, the stationary phase comprises a cyanophase silica material. Water, which can be detrimental to the main second separation, can also be retained on this precolumn.

The mobile phase carries the remaining, non-adsorbed constituents of the sample to optional second precolumn 3 comprising an adsorbent stationary phase chosen to eifectively adsorb a further constituent(s) of the sample, either a different hydrocarbon group of interest, a nonabsorbed constituent of the first hydrocarbon group or an incidental constituent of the sample to be discarded. In a preferred embodiment of the invention in which polar compounds of relatively low polarity and water are removed from the sample by adsorption on the second precolumn, the stationary phase comprises deactivated silica gel.

The mobile phase carries the remaining, non-adsorbed constituents of the sample via ports a and b of second 6-port switching valve 14 to a third chromatography column 4. In a preferred embodiment of the invention, column 4 will contain a stationary phase effective for adsorbing an aromatic constituent group and eluting a saturated constituent group and elemental sulfur. A suitable stationary phase for this column comprises activated silica.

The eluting saturated constituent group and elemental sulfur are passed via ports b and c of valve 11 to a detector for monitoring a property of the group. Any detecting means capable of monitoring the constituent of interest can be used. A preferred detector for the saturated constituent group is a differential refractometer. A preferred detector for the elemental sulfur constituent is an ultraviolet light absorbance detector, which can be calibrated, as is known in the art, by the injection of known quantities of elemental sulfur and measurement of the response of the UV detector. The detectors can be connected in series if desired as shown in the drawing of FIG. 1.

After the elution of the sulfur constituent and the saturated group constituent from column 4 and the detection of these constituents by the detectors, as can be observed by the return to baseline of a signal from the detectors being recorded, both valves are switched so as to first pass a mobile phase liquid, preferably hexane in the system described, from its reservoir via ports a and b of valve 11 through column 4 so as to remove any adsorbed aromatic constituent groups. The mobile phase carries the aromatic constituent phase via ports b and c of valve 14 and ports d and c of valve 11 to a detector effective for detecting a property of the aromatic constituent group representative of its presence, such as a diiierential refractometer or an ultraviolet absorbance detector.

The polar constituents can be removed from precolumns 2 and 3 by passing a suitable mobile phase liquid such as methylene chloride from its reservoir via ports e and f of valve 11 and f and a of valve 14 through the stationary phases of precolumns 3 and 2 and, via ports e and d of valve 14, to detection and/or collection means 8. The polar constituents can be collected and quantitatively studied by gravimetric means. For speed and convenience, the backflushing of column 4 for aromatic constituents and precolumns 2 and 3 for polars can be carried out simultaneously.

Backflushing can be carried out by switching valves 11 and 14 so as to permit flow of a backflush fluid from fluid reservoir to sample collection means 8 via line 9 and through the selected separations zone. The system is shown in the forward flow mode.

After collection of the data, the system is flushed with a suitable iluid to rid the columns of sample residues.

The fractions of interest can be recovered, for later evaluation if desired, in any suitable fraction collection system (not shown), as is known in the art. The elemental sulfur constituent can be directly determined quantitatively by comparing the detector response, in terms of peak area for example, with a calibrated ultraviolet absorance response curve. The aromatics, saturates and polars are determined gravemetrically fro the collected fractions. The results of the analysis, including the calculated recovery factor, the relative quantities of the various constituent groups, and the amount of elemental sulfur, are used to assess the oil or rock under study.

The process is generally carried out under medium-pressure conditions, but high-pressure chromatography can be used with appropriate adjustments of column length, sample size, and other conditions. Operation at ambient temperature is acceptable.

In obtaining best results from the invention analytical method, it is desirable to delay the backflushing of the precolumn(s) until the elution of the elemental sulfur constituent from main column 4 and the detection and recording of a peak representative of its quantity in the sample. This can be accomplished by appropriate timing of the 6-way valves shown in FIG. 1. A microprocessor can be used to activate the valves so as to delay the backflushing process until after elution of the elemental sulfur peak and to optimize the sequencing and timing of the system.

The invention method and apparatus enable the rapid and efficient analysis of an organic sample of matter for multiple organic constituents and elemental sulfur in a single process.

EXAMPLE 1

The apparatus employed for the described analysis is automatically controlled by a Perkin-Elmer Sigma 1B data station through an interface with a valve control unit, fraction collector, and chart recorders. Solvent reservoirs for carrier liquids hexane and methylene chloride are both connected to a pump, with the n-hexane reservoir feeding into a separate pump, which feeds into the automatic sample injector and ultimately into the differential refractometer detector. The output of the sample injector is connected to a first port of a switching valve. Pneumatic air lines are connected to each of the valves and to a valve control unit which is monitored and operated by a signal from the Perkin-Elmer Sigma 1B Data Station. An electronic recorder is connected to each of the detectors to provide a written record of the analysis.

The analytical system includes a Perkin-Elmer Sigma 1B Data Station, a P.E. Sigma 15 lnterface, a valve control unit containing six Skinner type B13DK1150 solenoid valves connected as known in the industry to operaie pneumatic valves, two Applied Automation model 10 pneumatic actuated valves, and, three stainless steel packed columns, a Waters Intelligent Sample Processor 710B (WISP), a Perkin-Elmer series 2 LC pump unit, a three-port Valco rotary valve, a Glenco 5480 ultraviolet detector with a 254 nanometer wavelength filter, a Waters Differential Refractometer R410 detector, a Perkin-Elmer 024 two-pen recorder, and optionally an Isco Foxy model 2200 fraction collector.

All samples are deasphaltened prior to injection. Hexane is then used to dilute the sample. The sample size is determined prior to injection using either volumetric or gravimetric methods which are well known in the industry.

Figure 2:
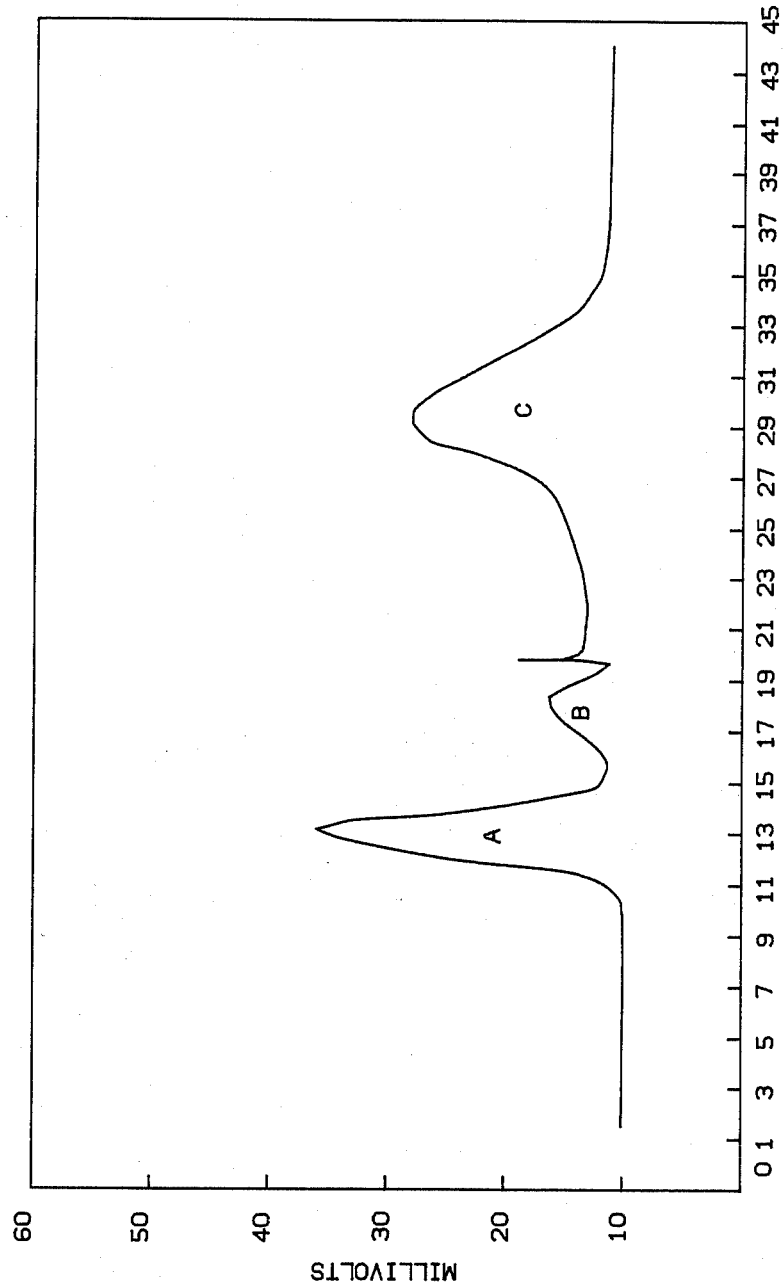
FIG. 2 is a chromatogram showing the differential refractometer response for a liquid sample analyzed according to the invention method.

The analysis of the sample requires the use of two mobile phases, n-hexane and methylene chloride as the sample solvent transporting means. The pumps used to feed the solvents operate at a rate of 5 mL/min flow. The solvents used were n-hexane and methylene chloride (by Burdick & Jackson) UV grade solvents, filtered and degassed at least several hours prior to use. The automatic injection system (WISP) is capable of injecting multiple samples automatically. The WISP also signals the Perkin-Elmer Sigma 1B data station to begin the timed-event control of the run. n-hexane solvent passes through the injector sweeping a sample to the first port of a switching valve. In the initial switching mode the first switching valve is positioned to provide fluid passage between ports a and f, ports e and d, and ports e and b, and the second switching valve is positioned to provide fluid passage between ports a and b, ports c and d, and ports e and f. The sample is passed in the n-hexane carrier to the first column of a series of precolumns. The first precolumn contains a cyanophase silica (All Tech RSIL prep-CN(25-40$\mu$) 9 mm internal diameter and 8" length packed stainless steel column). The first precolumn is used to retain the majority of polar compounds. The sample then enters the second precolumn, which contains a deactivated silica gel (deactivated EM SiO$_2$ gel 100 (63-200$\mu$) 11 mm internal diameter and 3½" length SS column; deactivation in bulk in a furnace, Initially at 300° C., heated to 650° C. followed by a two-hour hold, cooied and stored in a vacuum dessicator). The second precolumn is used to retain the less polar compounds not retained on the first precolumn. It also serves as a guard column for the main separation column by absorbing water. The sample components eluting from the precolumns are passed through the second selector valve into the main separation column which comprises a 26" long and 9 mm diameter activated EM SiO$_2$ gel 60 (40-63$\mu$; activated in situ at 120° C. in a tube furnace under nitrogen flow) stainless steel column. This is an activated silica gel and is used to separate the saturates from the aromatics and elemental sulfur. The saturates and elemental sulfur, eluting separately from the main column ahead of the aromatics, are directed to the detectors which are connected in series for recording. The record of the saturates is seen in FIG. 2 as peak A of the differential refractometer detector response curve. The elemental sulfur peak is seen as peak B of the differential refractometer response curve FIG. 2 and as peak B of the UV detector response curve in FIG. 3. The UV curve is used to quantitatively determine sulfur, since it is sulfur responsive. Prior to the elution of the aromatics from the main separation column both selector valves are switched such that opposite adjacent ports are in fluid communication. In this mode solvent from the sample injection system is directed in the reverse direction through the main separation column, which passes the aromatics through the selector valves to the detectors. At the same time the second solvent is directed in the reverse direction through the precolumns to flush out the polar components collection. The aromatic hydrocarbon peak is seen as peak C of the differential refractometer detector and UV detector response curves in FIG. 2 and FIG. 3, respectively. After the elution of the aromatics through the detectors and collection of the polar compounds, a n-hexane solvent is passed to rinse the precolumns. Additional analyses can be performed on the collected samples if desired.

Figure 3:
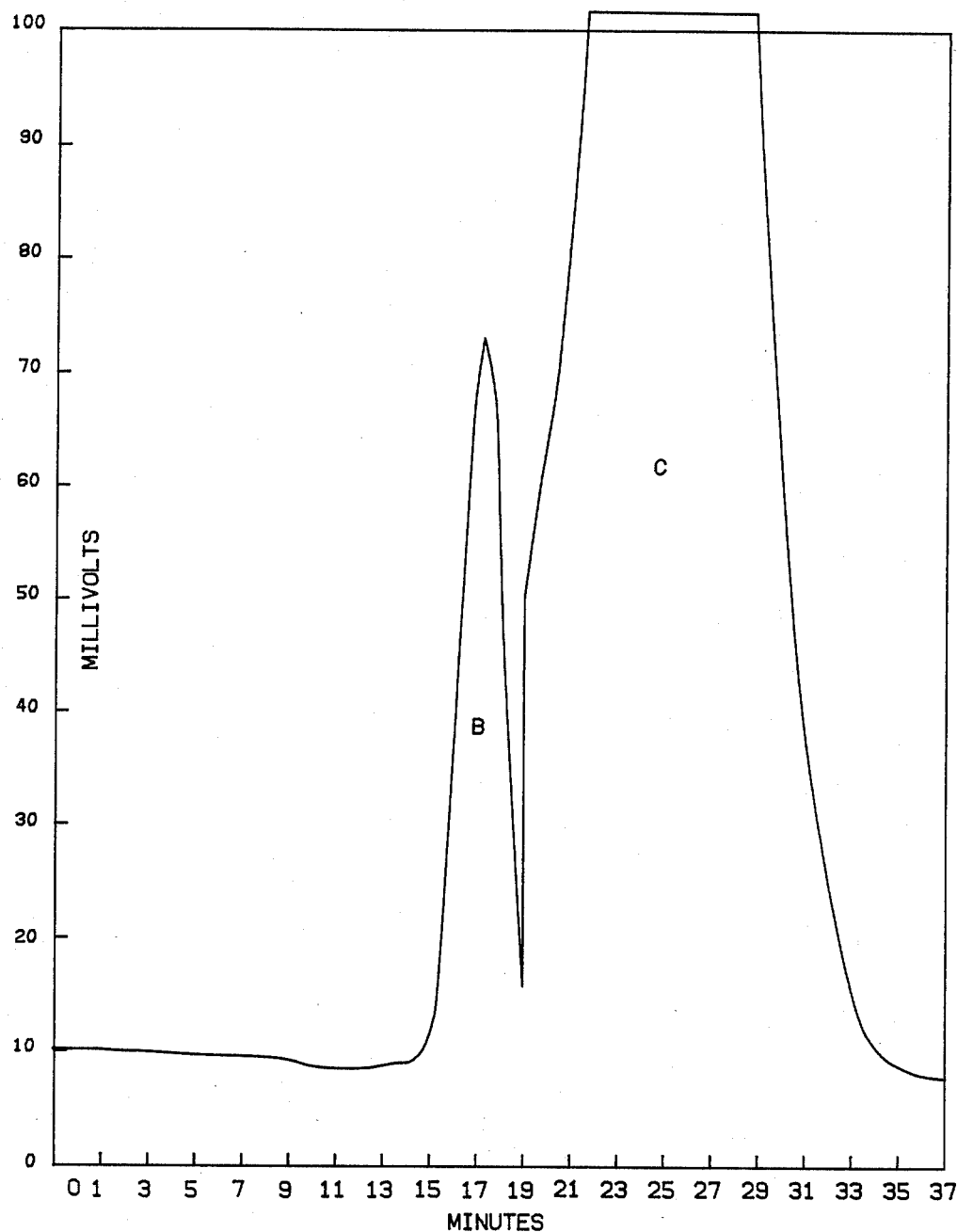
FIG. 3 is a chromatogram showing the ultraviolet absorbance detector response for a liquid sample analyzed according to the invention method.

The chromatogram of FIG. 2 and FIG. 3 are from a 25.95 mg sample of asphaltene free rock extract containing 5.80 mg saturated hydrocarbons eluting between 8 and 14 minutes, 0.73 mg elemental sulfur eluting between 13.8 and 19 min., 7.51 mg aromatic hydrocarbon eluting between 19 and 44 min. and 11.65 mg polar compounds eluting between 19 and 44 min. The aromatics and sulfur were collected together and the aromatics concentration deiermined by difference. The polar compounds collected while backflushing are determined by weight. The normalized weight percent (normalized in reference to the asphaltene-containing sample) of the compounds according to the chromatogram are: saturates 22.3, aromatics 26.2, polars 44.7 and elemental sulfur 2.7%. There was also a 4.1% asphaltene content in the original sample.

That which is claimed is:

1. A method for analysis of a liquid sample of matter comprising a first organic constituent, a second organic constituent and an elemental sulfur constituent, the method comprising:

passing the sample of matter in a mobile phase through a first separations zone comprising a stationary phase under conditions effective for the retention of essentially all of the first organic constituent in the first separations zone;

passing an effluent comprising the second organic constituent and the elemental sulfur through a second separations zone under conditions effective for the separation of the second organic constituent from the elemental sulfur constituent;

removing the second organic constituent from the second separations zone and detecting a property of the second organic constituent;

removing the elemental sulfur constituent from the second separations zone and determining a property of the elemental sulfur constituent; and removing the first organic constituent from the first separations zone and determining a property of the first organic constituent.

2. The method of claim 1 in which the first separations zone comprises a liquid chromatography column and the second separations zone comprises a liquid chromatography column.

3. The method of claim 2 in which the property of the second organic constituent is detected by passing the second organic constituent to a differential refractometer detector.

4. The method of claim 1 in which the first organic constituent is removed from the first separations zone by backflushing a liquid solvent for the first organic constituent through the first separations zone.

5. The method of claim 4 in which the first organic constituent is backflushed to an ultraviolet absorbance detector for detection of the property of the iirst organic constituent.

6. The method of claim 5 in which the first organic constituent is at least one polar chemical compound and the second organic constituent is selected from aromatic compounds and saturated organic compounds.

7. A method for analysis of a liquid sample of matter containing a first organic constituent comprising polar organic compounds, a second organic constituent comprising saturated organic compounds, a third organic constituent comprising aromatic organic compounds, and an elemental sulfur constituent, the method comprising:
(a) passing the liquid sample in a liquid mobile phase through a first separations zone comprising at least one adsorbent stationary phase under conditions effective for retaining essentially all of the first organic constituent in the first separations zone, to produce an effluent comprising the second organic constituent, the third organic constituent and the elemental sulfur;
(b) passing said effluent through a second separations zone comprising at least one adsorbant stationary phase under conditions effective for separating the second organic constituent, the third organic constituent and the elemental sulfur;
(c) passing the second organic constituent from the second separations zone and determining a property of the second organic constituent;
(d) passing the elemental sulfur constituent from the second separations zone and determining a property of the elemental sulfur constituent representative of its quantity;
(e) backflushing the second separations zone with a liquid under conditions effective for removing the third organic constituent from the second separations zone and determining a property of the third organic constituent;
(f) backflushing the first separations zone with a liquid under conditions effective for removing the first organic constituent from the first separations zone, and determining a property of the first organic constituent.

8. The method of claim 7 in which the first separations zone comprises at least one chromatography column packed with an adsorbent material comprising a cyanophase silica material.

9. The method of claim 8 in which the property of the first organic constituent is detected by an ultraviolet absorbance detector.

10. The method of claim 7 in which the second separations zone comprises at least one chromatography column packed with an adsorbent material comprising activated silica.

11. The method of claim 7 in which the property of the second organic constituent is detected by a differential refractometer detector.

12. The method of claim 7 in which the backflushing of the first and second separations zones is effected after essentially all of the elemental sulfur constituent is passed from the second separations zone.

13. The method of claim 7 in which the liquid sample is selected from petroleum fractions and oil shale extracts.

14. Apparatus for analysis of a sample of matter coniaining a first organic constituent comprising polar organic compounds, a second organic constituent comprising unsaturated organic compounds, a third organic constituent comprising aromatic organic compounds, and an elemental sulfur constituent, the apparatus comprising:
a first separations zone comprising at least one adsorbent stationary phase for retaining the first organic constituent and eluting the second organic constituent, the third organic constituent and the elemental sulfur constituent;
in liquid flow communication with the first separations zone, a second separations zone comprising at least one adsorbent stationary phase for retaining the third organic constituent and for eluting separately the second organic constituent and the elemental sulfur constituent;
in flow communication with the second separations zone, means for detecting a property of the second organic constituent;
in flow communication with the second separations zone, means for detecting a property of the elemental sulfur constituent representative of its quantity;
in backflow communication with the iirst separations zone, means for detecting the first organic constituent;
in backflow communication with the second separations zone, means for detecting a property of the third organic constituent.

15. The apparatus of claim 14 in which the first and second separations zones each comprise a liquid chromatography column packed with an adsorbent material.

16. The apparatus of claim 15 in which the means for detecting a property of the elemental sulfur constituent is an ultraviolet adsorbance detector.

17. The apparatus of claim 14 in which the means for detecting a property of the second organic constituent is a differential refractometer.

18. The apparatus of claim 15 in which the first separations zone comprises a liquid chromatography column packed with a cyanophase silica material.

19. The apparatus of claim 15 in which the second separations zone comprises a liquid chromatography column packed with activated silica.

20. The apparatus of claim 14 further comprising control means for sequencing and timing forward and referse flow through the first and second separations zones.

* * * * *